(12) United States Patent
Song et al.

(10) Patent No.: US 8,530,158 B2
(45) Date of Patent: Sep. 10, 2013

(54) SYSTEM AND METHOD FOR PROCESSING A BIOLOGICAL SAMPLE

(75) Inventors: Maengseok Song, Burlingame, CA (US); Achim Karger, Foster City, CA (US); Patrick Kinney, Hayward, CA (US)

(73) Assignee: Life Technologies Corporation, Carlsbad, CA (US)

( * ) Notice: Subject to any disclaimer, the term of this patent is extended or adjusted under 35 U.S.C. 154(b) by 83 days.

(21) Appl. No.: 13/104,304

(22) Filed: May 10, 2011

(65) Prior Publication Data

US 2011/0275125 A1    Nov. 10, 2011

Related U.S. Application Data

(60) Provisional application No. 61/333,203, filed on May 10, 2010.

(51) Int. Cl.
| | | |
|---|---|---|
| *C12Q 1/68* | (2006.01) | |
| *C12P 19/34* | (2006.01) | |
| *C12M 1/34* | (2006.01) | |
| *C12M 3/00* | (2006.01) | |

(52) U.S. Cl.
USPC ....... 435/6.1; 435/6.11; 435/91.1; 435/287.2; 977/704; 977/728; 977/773

(58) Field of Classification Search
USPC .................. 435/6.1, 6.11, 91.1, 283.1, 287.1, 435/287.2; 436/94, 501; 536/23.1, 24.3, 536/24.33; 977/704, 728, 773; 422/50, 68.1
See application file for complete search history.

(56) References Cited

U.S. PATENT DOCUMENTS

| | | |
|---|---|---|
| 3,941,317 A | 3/1976 | Kanor |
| 7,323,305 B2 | 1/2008 | Leamon et al. |
| 7,534,560 B2 * | 5/2009 | Lu et al. .................. 435/6.12 |
| 7,575,865 B2 | 8/2009 | Leamon et al. |
| 7,638,276 B2 | 12/2009 | Griffiths et al. |
| 7,842,457 B2 | 11/2010 | Berka et al. |
| 7,927,797 B2 | 4/2011 | Nobile et al. |
| 2005/0287572 A1 | 12/2005 | Mathies et al. |
| 2008/0171400 A1 | 7/2008 | Cho et al. |
| 2008/0304720 A1 | 12/2008 | Chang et al. |
| 2009/0023189 A1 | 1/2009 | Lau et al. |
| 2009/0233814 A1 | 9/2009 | Bashkirov et al. |
| 2010/0261229 A1 | 10/2010 | Lau et al. |
| 2010/0261230 A1 | 10/2010 | Liu et al. |
| 2011/0087016 A1 | 4/2011 | Suo |

FOREIGN PATENT DOCUMENTS

| | | |
|---|---|---|
| WO | WO-2005/073410 | 8/2005 |
| WO | WO-2010/117456 | 10/2010 |
| WO | WO-2010/117457 | 10/2010 |
| WO | WO-2010/117461 | 10/2010 |

OTHER PUBLICATIONS

PCT/US2011/035894 Internatonal Search Report.
PCT/US2011/035894 Written Opinon.
PCT/US2011/035894 International Preliminary Report on Patentability.

* cited by examiner

*Primary Examiner* — Frank Lu (57) ABSTRACT

Systems and methods for processing a biological sample are provided herein. For example, the system can be configured to deaggregate/declump a sample before, during, and/or after sample preparation and/or sample analysis. For example, the system can include a deaggregation device/system in communication with, for example, a nucleic acid amplification process (e.g., an ePCR system). Various embodiments of the deaggregation device are provided herein. For example, in some embodiments, the deaggregation device can include a valve, a valve manifold, a conduit, a channel, or some combinations thereof.

18 Claims, 5 Drawing Sheets

SYSTEM AND METHOD FOR PROCESSING A BIOLOGICAL SAMPLE

PRIORITY & RELATED APPLICATIONS

This application claims priority pursuant to 35 U.S.C. §119 to U.S. Provisional Patent Application Ser. No. 61/333,203, entitled "On-Instrument Declumping of Emulsion PCR Microsphere Aggregates By Passage Through a Pump Valve Manifold or Channel," filed on May 10, 2010, the entirety of which is incorporated herein by reference.

FIELD

The present disclosure relates to devices, systems, and methods for processing a biological sample, in particular to processing an aggregated sample to produce a deaggregated sample.

INTRODUCTION

A number of biological sample analysis systems and methods include sample preparation steps as a precursor to analysis. For example, sequencing of nucleic acids can include amplification of nucleic acid templates in order to obtain a large number of copies (e.g., millions of copies) of the same template.

A variety of nucleic acid amplification techniques, including, for example, the polymerase chain reaction, are commonly utilized to generate sufficiently large DNA populations suitable for detection or analysis. Some Next Generation Sequencing platforms can utilize emulsion-PCR ("ePCR") techniques and systems for providing amplified templates. In such amplification methods, a plurality of biological samples (e.g., nucleic acid samples tethered to microparticles) can be individually encapsulated in microcapsules of an emulsion (e.g., an aqueous component including, for example, a microparticle, template, reagents, and enzymes being encapsulated in oil) and PCR amplification can be conducted on each of the plurality of encapsulated nucleic acid samples simultaneously. Such microcapsules are often referred to as "microreactors" since the amplification reaction occurs within the microcapsule.

SUMMARY

Systems, devices, and methods for processing biological samples are provided herein. For example, various embodiments of processing an aggregated sample to produce a deaggregated sample are provided herein. Virtually any type of biological sample is within the spirit and scope of the present disclosure. For example, the sample can include nucleic acids such as DNA or RNA, proteins, peptides, carbohydrates, lipids, and other biological molecules or substances. The sample can also be whole cells or cell suspensions. In the case of nucleic acids, the sample can be nucleotides, oligonucleotides, polynucleotides, and the like. The sample can also be in the form of microparticles, beads, or other solid, semi-solid, or gel supports having a biological molecule, substance, or cell tethered (or otherwise attached) to it. The presently disclosed embodiments can also be incorporated or otherwise utilized with virtually any type of biological system. For example, the system can be a sequencing system, a PCR system, an emulsion PCR system, a biological sample preparation system, a biological sample production system, and the like.

In some embodiments, the system, device, or method can be utilized to process (e.g., declump, deaggregate, etc.) a sample before, during, and/or after a procedure, such as, for example, a nucleic acid amplification procedure.

These and other features are provided herein.

DRAWINGS

The accompanying drawings, which are incorporated in and constitute a part of this specification, illustrate exemplary embodiments and together with the description, serve to explain various principles. The skilled artisan will understand that the drawings, described below, are for illustration purposes only. The drawings are not intended to limit the scope of the present disclosure in any way.

DESCRIPTION OF VARIOUS EMBODIMENTS

Systems, devices, and methods for processing biological samples are provided herein. For example, various embodiments of processing an aggregated sample to produce a deaggregated sample are provided herein. Virtually any type of biological sample is within the spirit and scope of the present disclosure. For example, the sample can include nucleic acids such as DNA or RNA, proteins, peptides, carbohydrates, lipids, and other biological molecules or substances. The sample can also be whole cells or cell suspensions. In the case of nucleic acids, the sample can be nucleotides, oligonucleotides, polynucleotides, and the like. The sample can also be in the form of microparticles, beads, or other solid, semi-solid, or gel supports having a biological molecule, substance, or cell tethered (or otherwise attached) to it. The presently disclosed embodiments can also be incorporated or otherwise utilized with virtually any type of biological system. For example, the system can be a sequencing system, a PCR system, an emulsion PCR system, a biological sample preparation system, a biological sample production system, and the like.

In some embodiments, the system, device, or method can be utilized to process (e.g., declump, deaggregate, etc.) a sample before, during, and/or after a procedure, such as, for example, a nucleic acid amplification procedure. In some embodiments, the system can deaggregate/declump a sample during a polynucleotide amplification procedure. For example, as indicated above, Next Generation Sequencing ("NGS") platforms can utilize various embodiments of an ePCR system or methodology. For example, some NGS systems can utilize an ePCR system where clonal oligo- or polynucleotides are produced on a plurality of microparticles. An emulsion PCR process can include one or more processing stages or modules wherein each stage or module can include various inputs and/or outputs. For example, in some embodiments, an initial input can include a plurality of microparticles, reagents (e.g., nucleic acids, nucleotides, and the like), enzymes, and other components, and an output can include a plurality of microparticles having clonal populations of nucleic acids attached to them.

One example of an emulsion PCR system is the EZ Bead™ System provided by Life Technologies Corp. of Carlsbad, Calif. Various embodiments of emulsion PCR systems are also disclosed in Assignee's co-pending U.S. patent application Ser. No. 12/756,547, entitled "System and Method for Preparing and Using Bulk Emulsion," filed on Oct. 14, 2010, U.S. patent application Ser. No. 12/756,589, entitled Column Enrichment of PCR Beads Comprising Tethered Amplicons, filed on Apr. 8, 2010, and U.S. patent application Ser. No. 12/756,783, entitled System Comprising Dual-Sided Thermal Cycler and Emulsion PCR in Pouch," filed on Apr. 8, 2010, the entirety of these applications being incorporated herein.

While the following discussion exemplifies the inventive process in the context of ePCR, those skilled in the art will appreciate that the present disclosure includes, and the inventive process can be applied to, other kinds of nucleic acid amplification processes and other biological sample processing.

Applicants have found that in automated and manual emulsion-based PCR systems and methods, as well as other systems and methods utilizing small particulates or beads in their analytical workflow, problems can arise with respect to sample or particle aggregation. For example, aggregation or clumping can lead to blocking or clogging of fluidic lines. Also, aggregation or clumping can inhibit a sample's ability to adequately react with a reagent. That is, in an efficient process, each or most of the samples can be allowed to react with reagent(s) introduced into the system. However, in the case of an aggregated sample, portions of the sample, such as that portion entrapped within the aggregate, may be inhibited or prevented entirely from reacting with the reagent(s). Similarly, some ePCR systems, as well as other biological processing systems, can include wash steps where unwanted materials can be washed away from wanted materials (e.g., samples) during one or many processing steps. However, aggregated samples can make it difficult or even impossible to adequately wash away unwanted materials as these impurities can become trapped or ensnared within the aggregate. Wash steps can also be ineffective with aggregated samples as the entire surface area of each sample may be inaccessible to the wash reagents.

Further, ePCR systems can utilize various hybridization/binding steps which may be impeded as samples aggregate. For example, in some ePCR systems, some microparticles bind and amplify template (thus becoming a valuable sample) and some microparticles do not bind template (thus, in some procedures, becoming waste). That is, following ePCR, some procedures may require removing those particles having sample tethered thereto from those particles not having sample tethered thereto. More specifically, some systems can include processes for separating templated beads (i.e., beads having sample attached thereto) from non-templated beads (i.e., beads not having sample attached thereto). In some embodiments, such separation steps can include hybridizing "capture beads" or "enrichment beads" to templated particles in such a manner that only those particles having sample tethered thereto can become hybridized to the capture beads (e.g., the capture beads hybridize to the polynucleotide tethered to the microparticle). In some embodiments, the capture beads can be magnetic thereby allowing for these magnetic beads (and the sample attached thereto) to be easily separated from the non-templated particles by the application of a magnetic force. However, such processes are inefficient with aggregated samples because portions of the aggregated sample may never come into contact with the capture beads and thus quality sample (e.g., particles having nucleic acids tethered thereto) can be lost during the separation step merely because the templated particle never had an opportunity to react with the capture beads during the process.

Downstream analysis can also be hindered by aggregated samples produced by amplification procedures. For example, in some embodiments, microparticles can be deposited on a substrate (e.g., flowcell, multi-well plate, etc.) for analysis or imaging. During such analysis or imaging, clumped samples can result in inefficient processing and/or undecipherable data. For example, various NGS chemistries, such as pyrosequencing, sequencing-by-synthesis, and ligation sequencing, process samples on a substrate by introducing various reagents to samples and detecting signals resulting from the samples which can be indicative of some information relating to the samples. If samples are clumped together or aggregated on the substrate, some portion of the sample (e.g., some portion of biological sample tethered to some portion of the microparticles) may be prevented from having the opportunity to react with the reagents (e.g., signal-emitting hybridization tags) being introduced to the samples on the substrate.

Additionally, NGS procedures can periodically image the samples on the substrate to derive data from each or most samples. If the samples are aggregated together, it may be difficult or impossible to accurately identify and quantify signals emitted from samples. For example, in some embodiments, various fluorescent, luminescent, etc. tags can be hybridized to various samples and these hybridization events can be detected via various imaging systems. Similarly, in some embodiments, NGS platforms utilize chemiluminescent signals from samples wherein the detection system can correlate which sample provides which signal. However, if the samples are too close to one another, as would be the case with clumping, imaging/detection systems may have difficulty determining which emission signal and/or chemiluminescent signal is being emitted by which sample. This may result in the system or imaging software/hardware discarding data from otherwise useful samples. That is, in some NGS platforms and other biological sample imaging/detection systems, samples producing over-lapping or otherwise undecipherable signals will often be disregarded from the analysis and thus other-wise useful sample is lost and throughput is reduced.

Further, some systems require very accurate placement and delivery of samples to a substrate. Such accurate placement can be difficult with clumped samples. For example, some NGS techniques include delivering one or a few templated microparticles to wells of a multi-well plate (e.g., 1 particle per well). Such controlled delivery can be complicated when the sample is aggregated/clumped. Thus, it can be desirable to maintain a bead slurry with reduced amounts of bead aggregates throughout various stages of an ePCR process.

Approaches to declumpling of beads or particulates can include use of chemical coating agents (e.g., "bead block") which lessen the affinity of beads for one another. Bead aggregates can also be disrupted using energy transfer devices such as ultrasonic distruptors (sonicators). However, the above-described processes can often damage sample. That is, in the case of a nucleotide samples tethered to microparticles, high-energy sonication procedures can damage the biological sample (e.g., shearing of the sample) and/or disrupt the bond between the sample and the microparticle. Thus, while such processes can be utilized in combination with the presently disclosed embodiments, the presently disclosed embodiments reduce or eliminate damage to the sample during deaggregation.

In some embodiments, the presently disclosed system can include a deaggregation device. In some embodiments, the deaggregation device can be fluidically incorporated into some processing system (e.g., an amplification system). That is, the deaggregation device can be in fluid communication with an upstream system and/or in fluidic communication with some downstream system. In some embodiments, the deaggregation device can be a separate unit or system capable of receiving an aggregated sample from some distinct system and/or deliver a deaggregated sample to some distinct downstream unit.

The device can be any device capable of receiving an aggregated sample and outputting a deaggregated sample. For example, the deaggregation device can include at least one valve, valve manifold, component having an orifice or opening, channel, tube, and the like. In some embodiments, the device can include a valve manifold obtained from Kloehn Fluidic Systems of Las Vegas, Nev.

In some embodiments, the deaggregation device can include a pre-determined dimension selected to optimize deaggregation properties of the device. For example, in some embodiments, a length and/or diameter of some portion of the deaggregation device can be selected in order to optimize deaggregation of the sample. In some embodiments, the deaggregation device can include multiple openings, channels, and the like such that an aggregated sample can be divided into a plurality of sub-samples as the sample moves through the deaggregation device. In some embodiments, the deaggregation device can include a plurality of devices in series such that a sample passes through, for example, a series of valves. In some embodiments, the system can be configured such that samples are repeatedly passed through the same device (e.g., valve).

In some embodiments, the deaggregation device includes an opening(s) or channel(s) of a pre-determined diameter which can be selected to facilitate the deaggregation process. The diameter can be constant or variable. In some embodiments, the diameter of the passage/opening of the valve manifold, orifice, or channel can be between about 1 micron and about 5000 microns. In some embodiments, the diameter can be between about 10 microns and about 5000 microns. In some embodiments, the diameter can be between about 200 microns and about 2000 microns. In some embodiments, the diameter can be between about 500 microns and about 1000 microns. Those skilled in the art will appreciate that various other diameters and diameter ranges are within the spirit and scope of the present disclosure.

In some embodiments, various system parameters can be selected and optimized in order to maximize declumping/deaggregation as sample passes though the deaggregation device. For example, in some embodiments, a flow-rate of the sample through the system and/or through the deaggregation device can be optimized relative to the diameter and/or length of some opening, channel, valve, valve manifold, tubing, etc. of the deaggregation device. Those skilled in the art will appreciate that various other system parameters, such as sample density, sample viscosity, and the like, can also be optimized to facilitate sample declumping.

The deaggregation device can be fabricated or formed from various materials. In some embodiments, the device can be fabricated from (or include some coating of) a non-reactive/non-inhibitory material thereby reducing or eliminating sample loss as sample passes through the device. For example, in some embodiments, the deaggregation device can include a valve and/or channel and at least a portion of the interior of the valve and/or channel can include a non-reactive/non-inhibitory material. In some embodiments, the non-reactive/non-inhibitory material can be selected from the group consisting of metal, glass, plastic, polymer-coated, ceramic, silicon, and combinations thereof.

In some embodiments, the presently disclosed systems and methods can be adapted for different particle sizes and/or densities/concentrations by increasing or decreasing the diameter of openings or pathways in, for example, a valve, channel, and/or valve manifold. In some embodiments, a desired diameter for the opening may be determined on the basis of the increase in velocity of the fluid or bead slurry as the samples passes through the opening, channel, valve, conduit, or the like. For example, using a syringe barrel having a diameter of approximately 14.6 mm with a fluid supply tubing diameter of approximately 0.030 inches suggests that when the liquid is pumped thru a valve manifold fluid from the syringe, velocity can be increased about 340 fold. In the case of a pump, a typical Kloehn pump speed setting of 6 (2400 steps per second, flow rate 1000 ul/s) the use of a piston having a 10 ml syringe provides a flow-rate of about 6 mmls.

Figure 1:
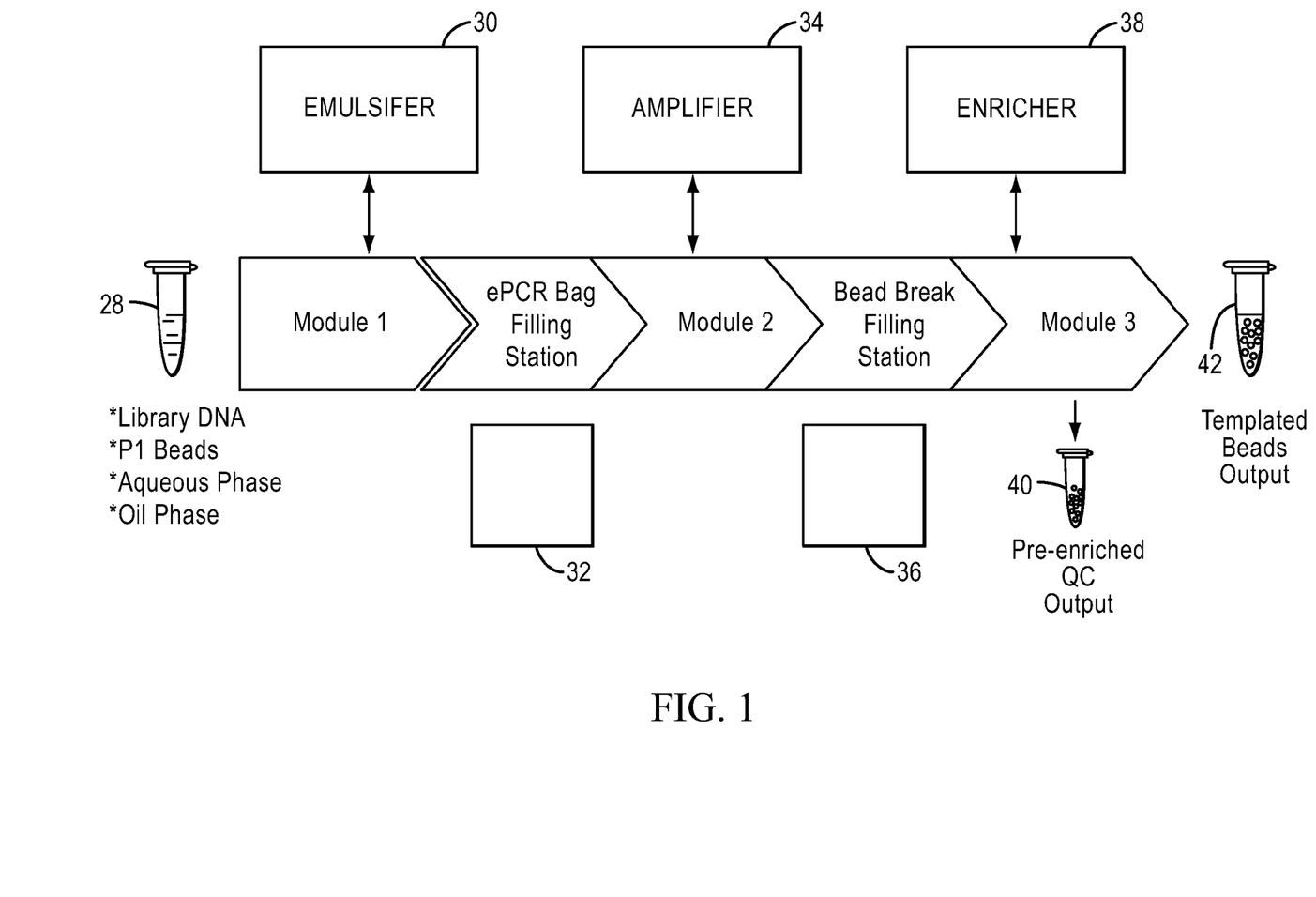
FIG. 1 is a flow diagram of an embodiment of a sample processing workflow.

FIG. 1 shows various steps/stages which can be included with some embodiments of the present disclosure. While these steps/stages relate to ePCR, various other such systems are within the spirit and scope of the present disclosure. For example, as shown in FIG. 1, the workflow can progress from an emulsion generation to sample enrichment step. That is, an emulsion generation module 30 (also shown in FIG. 1 as Module 1) can include a step or steps of forming microreactors discussed above within an oil or oil-like material. As discussed above, once the emulsion is formed, each microreactor can include one microparticle and various reagents or inputs 28. In some embodiments, the input 28 can include an aqueous phase master mix which can include, for example, water, dNTPs, and DNA polymerase.

In some embodiments, following some embodiments of an emulsion formation procedure, the emulsion can be transferred, e.g., poured, into a bag using an ePCR bag filling station 32. After filling, the bag can be closed or sealed, for example, by heat-sealing. In some embodiments, the bag and its contents can then be thermally cycled using, for example, some embodiment of an amplification module 34 (also shown in FIG. 1 as Module 2). In some embodiments, following thermocycling, the contents of the bag can be poured or otherwise transferred into an emulsion break vessel at an emulsion break filling station 36. In some embodiments, after breaking the emulsion to release, for example, the templated particles (i.e., those particles having polynucleotides tethered thereto) and non-templated particles (i.e., those particles not having polynucleotides tethered thereto) can be separated from one another such that the templated particles can be enriched relative to the non-templated beads. For example, this enrichment can be performed via using some embodiments of a bead enrichment module 38 (also shown in FIG. 1 as Module 3). In some embodiments, there can be two or more outputs of the system, including, for example, a first output 40 that includes a pre-enriched quality control output that can provide a user with information on bead clonality. In some embodiments, a second output 42 can be provided that includes templated beads that are ready for additional processing, for example, terminal transferase modification, deposition on a slide, multi-well plate, or in/on a flow cell, a combination thereof, or the like.

While the system described in connection with FIG. 1 comprises distinct modules, stations, and steps, it is to be understood that the system can comprise less or more modules and/or stations and that various modules and/or stations can be combined together. Furthermore, it is to be understood that the method can comprise fewer or more steps and that any of the steps described in connection with FIG. 1 can each independently be omitted or combined with one or more other steps.

Figure 2A:
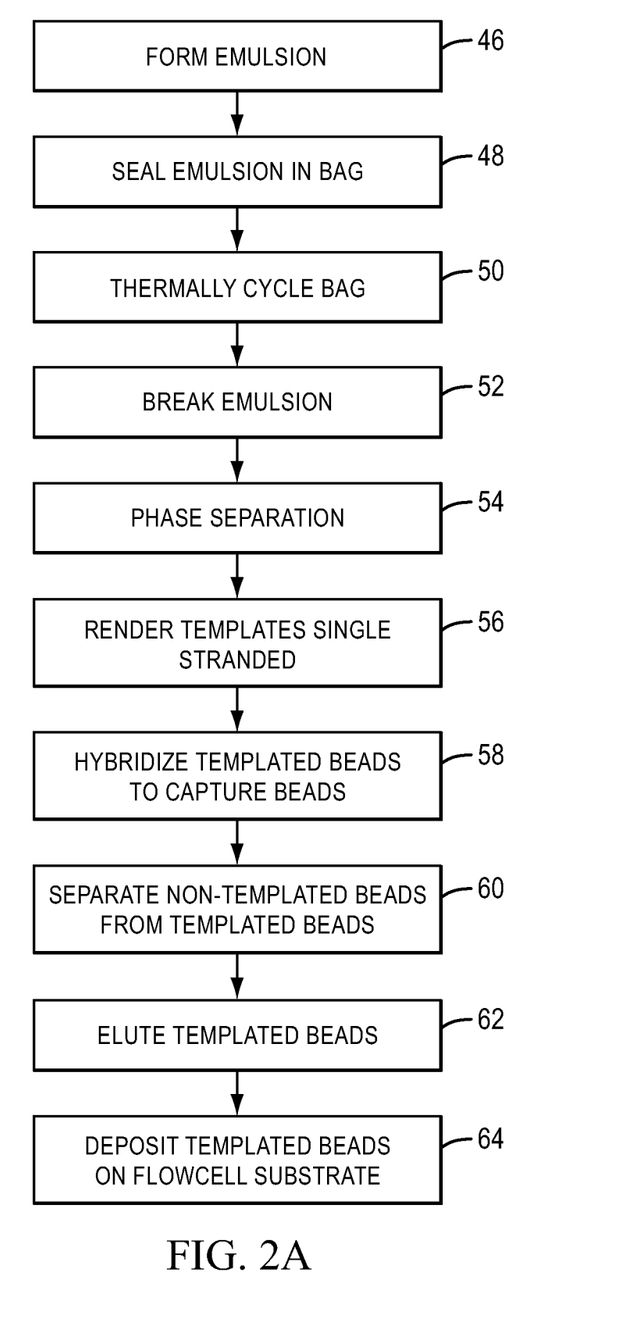
FIG. 2A is a process flow diagram illustrating various steps/systems associated with some embodiments of the present disclosure.

Similar to FIG. 1, FIG. 2A provides another representation of steps utilized by some embodiments of a ePCR system. For example, as with FIG. 1, the steps/modules represented in FIG. 2A can each be omitted, substituted, or combined with one or more other process steps. In some embodiments, a first step 46 of the method can comprise forming an emulsion. The emulsion can be formed according to any of the various embodiments of the present teachings and as described herein. In some embodiments, in a next step 48, the emulsion can be sealed in a bag. The sealed bag can then be thermally cycled as depicted by process step 50. In some embodiments, the thermal cycling can result in templated beads each comprising amplicons of a respective template tethered to a respective template-capturing particle. In some embodiments, the method can further comprise an emulsion breaking step 52 followed by a phase separation step 54, tailored to separate the template-capturing particles from the remainder of the emulsion (e.g., the non-templated microparticles). In some embodiments, a denaturing step 56 can be provided to render the templates tethered to the template-capturing particles, single stranded.

In some embodiments, the template particles bearing the single-stranded templates can be hybridized to capture/enrichment beads to form a capture complex, as depicted at step 58. In some embodiments, the templated particles captured in the capture complexes can be separated by non-templated beads in a separation step 60, for example, using a size-exclusion technique. In some embodiments, a step 62 can be provided wherein the templated beads are eluted from the capture complexes and are collected. In some embodiments, the collected templated beads can be deposited on/in a substrate (e.g., a flowcell, multi-well plate, etc.) or otherwise formed into an array in/on the substrate (e.g., one or more bead placed in all or substantially all wells of a multi-well plate).

During any of the stages or steps depicted in FIG. 1 and/or FIG. 2A, some embodiment of a deaggregation device or system can be incorporated into the system in order to process the sample passing therethrough. That is, some embodiment of the deaggregation device can be placed in fluidic communication between, for example, any consecutive steps such that the deaggregation device receives an aggregated sample, produces a deaggregated sample, and delivers (and/or somehow allows recovery of) the deaggregated sample downstream for further processing. The deaggregation/declumping step(s) can be performed at any time. For example, the step(s) can be performed before the first step of a procedure, at any point during the procedure, and/or at any point after the procedure or any step of the procedure. The declumping/deaggregation procedure can be performed one time or numerous times. In some embodiments, different declumping/deaggregation steps can be performed at the same or various points before, during, and/or after the procedure. Thus, those skilled in the art will appreciate that any number and/or type of deaggregation and/or declumping procedures having any number of steps can be performed any number of times and at any point(s) during any type of procedure (e.g., an emulsion PCR procedure).

Figure 2B:
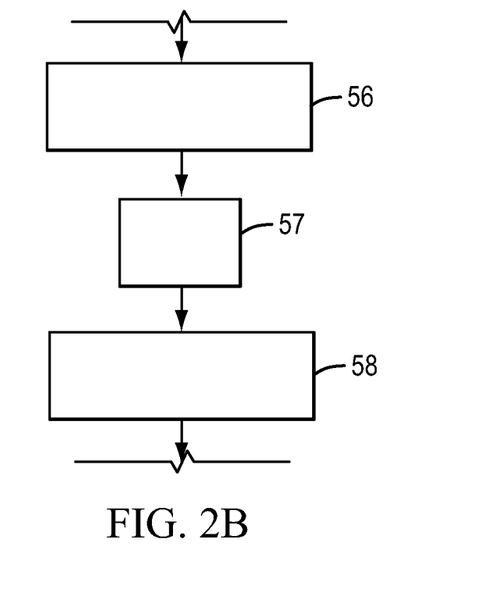
FIG. 2B is a process flow diagram illustrating various steps/systems associated with some embodiments of the present disclosure.

Referring to FIG. 2A, in some embodiments, a deaggregation/declumping step(s) can be performed between any of the representative steps. For example, in some embodiments, as shown in FIG. 2B, the deaggregation device/system 57 can be performed between "Render Templates Single Stranded" (Step 56) and "Hybridize Templated Beads to Capture Beads" (Step 58). In some embodiments, the deaggregation device/step can be performed, for example, any time or times following the emulsion break step 52. That is, declumping the sample following emulsion break can facilitate hybridization of the capture/enrichment beads to the templated particles.

Also, declumping post-emulsion break can facilitate the denaturing step 56 by helping to ensure that sample attached to each or a majority of the microparticles undergo the denaturing reaction and are not prevented from denaturing because they are trapped within an aggregated sample. Also, declumping prior to filtration 60 can facilitate filtration through some size-exclusion device because aggregated samples can potentially take a longer period of time to adequately pass through the filtering mechanism and could also potentially clog the filter. Also, deaggregation can facilitate elution of the capture/enrichment beads 62 from the templated particles because, similar to the denaturing step, a deaggregated samples can result in a larger portion of the sample undergoing the desired reaction as opposed to being prevented and/or hindered from reacting because the sample is trapped or restrained within the aggregate. Those skilled in the art will appreciate that declumping steps can also be introduced between any other steps of the workflow example of FIG. 1 and/or FIG. 2A (e.g., prior to the emulsion break).

Figure 2C:
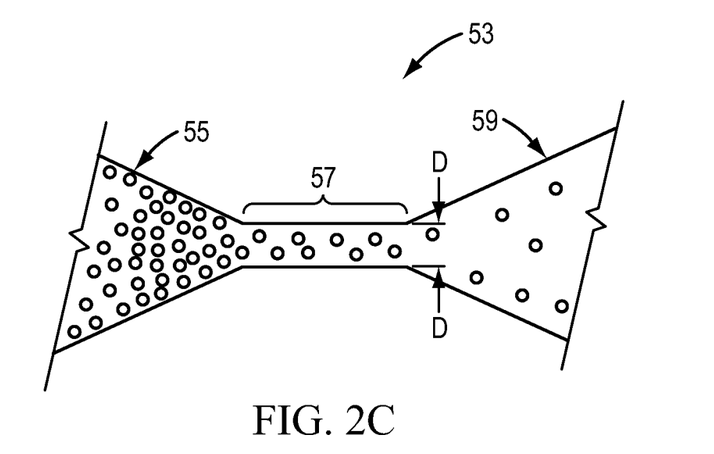
FIG. 2C is a representation of an aggregated sample entering an embodiment of a deaggregation device and a deaggregated sample exiting the deaggregation device.

FIG. 2C is a representation of some embodiments of a deaggregation device/step. For example, some biological system (e.g., ePCR, sequencing, etc) 53 can include an embodiment of a deaggregation device 57 in fluidic communication with an input stream 55 and/or an output stream 59. As shown, the input stream 55 can include an aggregated sample being introduced to the deaggregation device 57. In some embodiments, the deaggregation device 57 can have a diameter D smaller than that of at least one of the input/output channels 55, 59 such that passage therethrough is restricted. As shown, the decrease in diameter can result or at least facilitate deaggregation of the aggregated sample (e.g., beads having polynucleotides tethered thereto) as the sample moves from the input channel 55 to the output channel 59 through the deaggregation device 57.

As indicated above, the presently disclosed embodiments can be utilized in conjunction with other deaggregation processes such as chemical treatments and/or sonication. For example, during ePCR, various chemicals utilized to break an emulsion can have a side-effect of clumping the beads. In such cases, introducing water soluble detergent to the emulsion mixture may help prevent or avoid aggregation of the beads. However, processing of the emulsion break solution (or any suitable cell/particle/bead containing mixture, slurry, or composition) may involve one or more passages of the beads or bead slurry thru some embodiment of the presently disclosed deaggregation system or device (e.g., a conduit or channel system such as ceramic, metal or other material conduit or valve system having the appropriate dimensionality) at some optimized flow rate.

EXAMPLES

The following examples are illustrative and are in no way meant to limit the scope of the claims and/or disclosure in any way.

FIGS. 3A-3D and FIGS. 4A-4D provide data from experimental runs which illustrate the ability of some embodiments of the present disclosure to deaggregate an aggregated sample of particles.

Figure 3A:
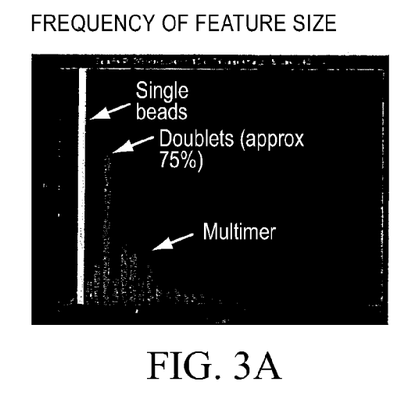
FIG. 3A is a chart relating to sample aggregation data from a control sample.
Figure 3B:
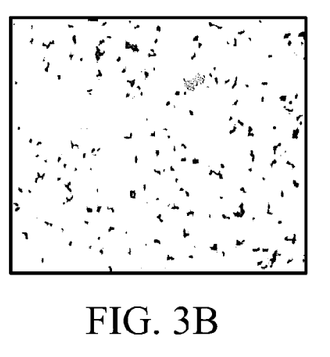
FIG. 3B is a representation of the data of FIG. 3A.
Figure 3C:
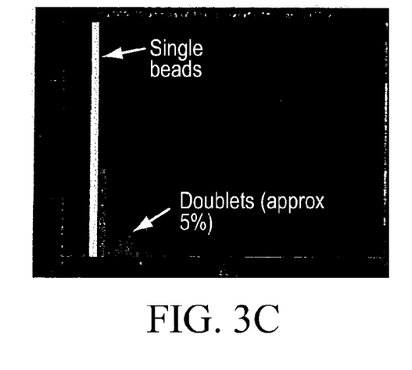
FIG. 3C is a chart relating to sample aggregate data following a deaggregation procedure in accordance with some embodiments of the present disclosure.
Figure 3D:
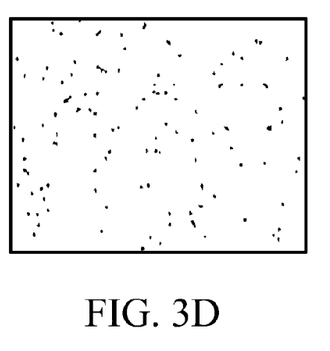
FIG. 3D is a representation of the data of FIG. 3C.

FIGS. 3A-3D provide an example of micron-sized ePCR beads following an emulsion break. Following the break, beads were collected on 0.45 um filter (Supor). The beads were then passed thru a ceramic valve pump manifold obtained from Kloehn Fluidic Systems of Las Vegas, Nev., and viewed under a microscope. FIG. 3A and FIG. 3B show results when the aggregated particles are not passed through a deaggregation device. FIGS. 3C and 3D show results when aggregated particles are passed through a deaggregation device, the Kloehn valve manifold. As depicted in the significant reduction in "doublets" between the data of FIG. 3A and FIG. 3C and the visually significant declumping/deaggregation evident by visually comparing the data of FIG. 3B and FIG. 3D, passage of the bead aggregate through the valve manifold in accordance with the methods described herein provides an efficient mechanism to increase the population of the single beads and to reduce the occurrence of aggregates (e.g., "doublets"). That is, following passage of the sample through the deaggregation device as depicted in FIG. 3C and FIG. 3D there is a marked improvement in the single bead population characteristics.

Figure 4A:
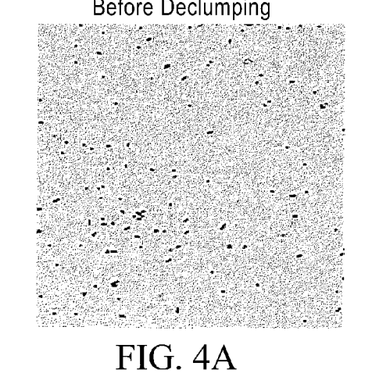
FIG. 4A is a representation of sample aggregate data from a control sample.
Figure 4B:
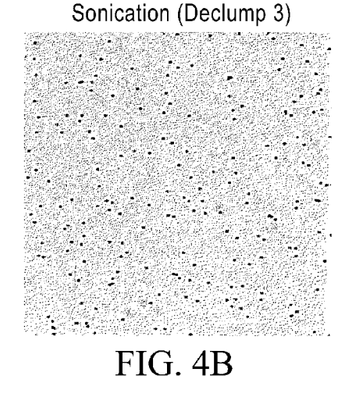
FIG. 4B is a representation of sample aggregate data following a sonication procedure.
Figure 4C:
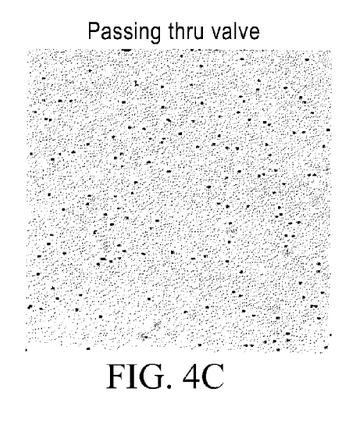
FIG. 4C is a representation of sample aggregate data following a deaggregation procedure in accordance with some embodiments of the present disclosure.
Figure 4D:
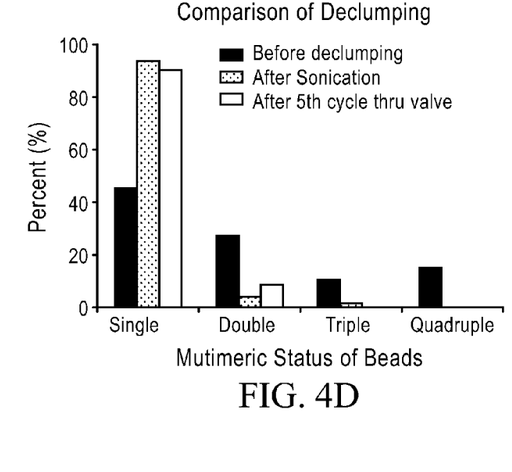
FIG. 4D is a chart which provides a comparison of sample aggregate distributions for a control procedure, a sonication procedure, and a deaggregation procedure in accordance with the present disclosure.

FIGS. 4A-4C provide data which allows for a comparison between processes not utilizing a declumping step (FIG. 4A), processes utilizing a sonication step for declumping (FIG. 4B), and processes using some embodiments of the present disclosure (FIG. 4C). FIG. 4D provides such a comparison between these distinct processes.

FIG. 4B provides data resulting from a declumping procedure performed with an ultrasonic instrument (e.g., Covaris with declump 3 according to SOLiD Sequencing System (Life Technologies of Carlsbad, Calif.)).

FIG. 4C provides data resulting from a declumping procedure performed by passing the aggregated sample through a ceramic valve pump manifold obtained from Kloehn Fluidic Systems of Las Vegas, Nev. In this example, bead aggregates were filtered using a 0.45 um syringe filter (Pall Life sciences, Acrodisc syringe filter, low protein binding, PN: 4614). Beads were declumped by pumping the beads into a syringe through the Kloehn valve and this was repeated for 5 cycles at a pump rate of approximately 1 ml/sec. Beads were then counted by plating beads (4000 beads/ul) on a slide using MetaMorph software package. FIG. 4D provides a comparison between the aggregated sample (FIG. 4A), de-aggregation via sonication (FIG. 4B), and deaggregation via a deaggregation device (FIG. 4C). The data presented in FIG. 4D further demonstrates the utility of the above-described teachings and the improvement in declumping efficiency to reduce multimeric units and achieve desirable enhanced single bead populations. Additionally, the data of FIG. 4D shows that the deaggregation device can provide results similar to sonication without the potential damage to sample which can result from such high-energy, sonication procedures.

It is to be understood that each of the publications referenced herein is independently incorporated herein in its entirety by reference.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, as illustrated by the range of from 1 to 5.

It is noted that, as used in this specification and the appended claims, the singular forms "a," "an," and "the," include plural referents unless expressly and unequivocally limited to one referent. As used herein, the term "include" and its grammatical variants are intended to be non-limiting, such that recitation of items in a list is not to the exclusion of other like items that can be substituted or added to the listed items.

It will be apparent to those skilled in the art that various modifications and variations can be made to the devices, systems, and methods of the present disclosure without departing from the scope its teachings. Other embodiments of the disclosure will be apparent to those skilled in the art from consideration of the specification and practice of the teachings disclosed herein. It is intended that the specification and examples be considered exemplary only.

What is claimed is:

1. A method for processing a plurality of microparticles in an aggregated sample, comprising:
    obtaining an aggregated sample comprising a plurality of microparticles, at least some of the microparticles having a polynucleotide tethered thereto, wherein the microparticles are aggregated in the aggregated sample;
    introducing the aggregated sample to a deaggregation device that includes at least one valve and at least one channel or a valve manifold and at least one channel so that a de-aggregated sample comprising the microparticles de-aggregated from the aggregated sample is produced; and
    recovering the de-aggregated sample from the deaggregation device.

2. The method of claim 1, wherein at least a portion of the microparticles includes a plurality of substantially clonal polynucleotides tethered thereto.

3. The method of claim 1, wherein the channel has a diameter.

4. The method of claim 3, wherein the diameter is between about 10 microns and about 5000 microns.

5. The method of claim 3, wherein the diameter is between about 200 microns and about 2000 microns.

6. The method of claim 3, wherein the diameter is between about 500 microns and 1000 microns.

7. The method of claim 1, wherein the introducing step is performed at least two times.

8. The method of claim 1, wherein the at least one valve is at least two valves.

9. The method of claim 1, wherein at least a portion of the deaggregation device includes a non-reactive/non-inhibitory material.

10. The method of claim 9, wherein the non-reactive/non-inhibitory material is selected from the group consisting of metal, glass, plastic, polymer-coated, ceramic, silicon, and some combination thereof.

11. The method of claim 1, wherein the at least one channel is a plurality of channels.

12. A method for processing a plurality of microparticles in an aggregated sample, comprising:
    obtaining an aggregated sample comprising a plurality of microparticles, at least some of the microparticles having a polynucleotide tethered thereto, wherein the microparticles are aggregated in the aggregated sample;
    introducing the aggregated sample to a deaggregation device that comprises at least one channel having a diameter between about 10 microns and about 5000 microns and at least one valve or the at least one channel and a valve manifold so that a de-aggregated sample comprising the microparticles de-aggregated from the aggregated sample is produced; and
    recovering the de-aggregated sample from the deaggregation device.

13. The method of claim 12, wherein at least a portion of the microparticles includes a plurality of substantially clonal polynucleotides tethered thereto.

14. The method of claim 12, wherein the deaggregation device includes a valve, a channel, a valve manifold, or some combination thereof.

15. The method of claim 12, wherein the diameter is between about 200 microns and about 2000 microns.

16. The method of claim 12, wherein the diameter is between about 500 microns and 1000 microns.

17. The method of claim 12, wherein at least a portion of the deaggregation device includes a non-reactive/non-inhibitory material.

18. The method of claim 17, wherein the non-reactive/non-inhibitory material is selected from the group consisting of metal, glass, plastic, polymer-coated, ceramic, silicon, and some combination thereof.

* * * * *